United States Patent
Giuffrida et al.

(10) Patent No.: US 10,966,652 B1
(45) Date of Patent: Apr. 6, 2021

(54) METHOD AND SYSTEM FOR QUANTIFYING MOVEMENT DISORDER SYSTEMS

(75) Inventors: Joseph P. Giuffrida, Hinckley, OH (US); Dustin A. Heldman, Shaker Heights, OH (US); Thomas O. Mera, South Euclid, OH (US)

(73) Assignee: Great Lakes NeuroTechnologies Inc., Cleveland, OH (US)

( * ) Notice: Subject to any disclaimer, the term of this patent is extended or adjusted under 35 U.S.C. 154(b) by 2734 days.

(21) Appl. No.: 13/152,963

(22) Filed: Jun. 3, 2011

Related U.S. Application Data

(63) Continuation-in-part of application No. 12/250,792, filed on Oct. 14, 2008, now abandoned.

(51) Int. Cl.
*A61B 5/00* (2006.01)
*G16H 40/60* (2018.01)
*G16H 20/10* (2018.01)

(52) U.S. Cl.
CPC .......... *A61B 5/4082* (2013.01); *G16H 20/10* (2018.01); *G16H 40/60* (2018.01)

(58) Field of Classification Search
CPC .............................................. G06Q 50/22–24
USPC ....................................................... 705/2–3
See application file for complete search history.

(56) References Cited

U.S. PATENT DOCUMENTS

| | | |
|---|---|---|
| 5,772,611 A | 6/1998 | Hocherman |
| 2004/0249422 A1* | 12/2004 | Gliner et al. .................. 607/58 |
| 2005/0234309 A1 | 10/2005 | Klapper |
| 2005/0240086 A1* | 10/2005 | Akay ............................. 600/300 |
| 2007/0053253 A1 | 3/2007 | Moore et al. |

(Continued)

OTHER PUBLICATIONS

CleveMed, "Kinesia", accessed on Jan. 11, 2011 and showing archive date of Aug. 5, 2007, accessed at: http://web.archive.org/web/20070718060543/www.clevemed.com/products/prod_all_p_kinesia.php.*

(Continued)

*Primary Examiner* — Robert A Sorey
(74) *Attorney, Agent, or Firm* — Brian Kolkowski

(57) ABSTRACT

A system and method for scoring movement disorder symptoms comprises a movement measurement data acquisition system and processing comprising kinematic feature extraction and an algorithm trained using Unified Parkinson's Disease Rating Scale (UPDRS) and Movement Disorder Society UPDRS (MDS-UPDRS) scores from skilled clinicians. The movement data acquisition system, or "movement measuring apparatus," may comprise sensors such as accelerometers or gyroscopes or may utilize motion capture and/or machine vision technology or various other methods to measure tremor, bradykinesia, gait and balance disturbances, dyskinesia, or other movement disorders in a subject afflicted with Parkinson's disease, essential tremor or the like. The method outputs, and system displays, a score that uses and inclusive 0-4 scale that correlates to the UPDRS and MDS-UPDRS, or to a particular component of the movement disorder such as speed, amplitude or rhythm, but has greater resolution and lower variability. In some embodiments, the system is used to diagnose and/or treat the patient by providing recommendations for treatment and/or by supplying treatment in the form of pharmaceutical drugs and/or electric stimulus as part of a closed-loop system.

15 Claims, 4 Drawing Sheets

(56) References Cited

U.S. PATENT DOCUMENTS

| | | | | |
|---|---|---|---|---|
| 2008/0312513 A1* | 12/2008 | Simon | ............... | A61B 5/16 600/300 |
| 2009/0192556 A1* | 7/2009 | Wu et al. | ............... | 607/3 |

OTHER PUBLICATIONS

CleveMed, "Kinetisense", accessed on Jan. 11, 2011 and showing archive date of Aug. 5, 2007, accessed at: http://web.archive.org/web/20071223064128/www.clevemed.com/products/prod_all_p_kinetisense.php.*

CleveMed, "Parkinsense", accessed on Jan. 11, 2011 and showing archive date of Aug. 5, 2007, accessed at: http://web.archive.org/web/20070625164609/www.clevemed.com/about_us/abtus_movementdisorders.htm.*

PR Newswire. "CleveMed Receives FDA Clearance to Market Wireless Movement Disorder Monitor", New York: May 1, 2007.*

Giuffrida, Joseph P., et al. "ParkinSense: A Wireless Movement Disorder Quantification System", Aug. 5, 2007.*

Goetz, Christopher G., et al. "MDS-UPDRS", Movement Disorder Society, Jul. 1, 2008.*

Christopher G. Goetz, M.D. and Glenn T. Stebbins, Ph.D., "Assuring interrater reliability for the UPDRS motor section: Utility of the UPDRS Teaching Tape", Movement Disorders, vol. 19, No. 12, pp. 1453-1456, 2004. United States.

FlexAble Systems, Inc. web site, http://www.managingtremor.com. Viewed Aug. 27, 2008.

Motus Bioengineering Inc. web site, http://www.motusbioengineering.com. Viewed Aug. 27, 2008.

M.P. Caligiuri and R.M. Tripp, "A portable hand-held device for quantifying and standardizing tremor assessment", Journal of Medical Engineering and Technology, vol. 28, No. 6, pp. 254-262, Nov./Dec. 2004. United States.

Arash Salarian et al., "Quantification of tremor and bradykinesia in Parkinson's disease using a novel ambulatory monitoring system", IEEE Transactions on Biomedical Engineering, vol. 54, No. 2, pp. 313-322, Feb. 2007. United States.

Arash Salarian et al., "An ambulatory system to quantify bradykinesia and tremor in Parkinson's disease", Proceedings of the 4th International IEEE EMBS Special Topic Conference on Information Technology Applications in Biomedicine, pp. 35-38, 2003. United Kingdom.

Ryuhei Okuno et al., "Finger taps movement acceleration measurement system for quantitative diagnosis of Parkinson's disease", Conference proceedings of the Annual International Conference of the IEEE Engineering in Medicine and Biology Society, Conference, Sep. 13, 2006, 6623-6626. New York, New York, United States.

Cleveland Medical Devices Inc. Kinesa User's Guide 2.0, Part No. 392-0014. Completed May 15, 2007.

Cleveland Medical Devices Inc. KinetiSense User's Guide Final, Part No. 392-0018. Completed Mar. 12, 2007.

Cleveland Medical Devices Inc. KinetiSense User's Guide Final, Part No. 392-0018. Completed Jun. 21, 2007.

Cleveland Medical Devices Inc. sales invoices (3), representing the earliest sales of Kinesia (international and domestic) and KinetiSense (domestic) products.

Dustin Heldman, et al., "The Modified Bradykinesia Rating Scale for Parkinson's Disease: Reliability and Comparison with Kinematic Measures," Movement Disorders. Apr. 29, 2011 (Epub ahead of print). United States.

A. Kishore, et al., "Unilateral versus bilateral tasks in early asymmetric Parkinson's disease: differential effects on bradykinesia," Movement Disorders, vol. 22, No. 3, pp. 328-333, Feb. 15, 2007. United States.

R.J. Dunnewold, et al., "Quantitative assessment of bradykinesia in patients with Parkinson's disease," Journal of Neuroscience Methods, vol. 74, No. 1, pp. 107-112, Jun. 6, 1997. Netherlands.

R.J. Dunnewold, et al., "Ambulatory quantitative assessment of body position, bradykinesia, and hypokinesia in Parkinson's disease," Journal of Clinical Neurophysiology, vol. 15, No. 3, pp. 235-242, May 1998. United States.

J.P. Giuffrida, et al., "Clinically deployable Kinesia technology for automated tremor assessment," Movement Disorders, vol. 24, No. 5, pp. 723-730, Apr. 15, 2009. United States.

T. Boraud, et al., "Quantification of motor slowness in Parkinson's disease: correlations between the tapping test and single joint ballistic movement parameters," Parkinsonism Related Disorders, vol. 3, No. 1, pp. 47-50, Jan. 1997. England.

* cited by examiner

METHOD AND SYSTEM FOR QUANTIFYING MOVEMENT DISORDER SYSTEMS

CROSS REFERENCE TO RELATED APPLICATIONS

This patent application is a continuation-in-part of currently pending U.S. patent application Ser. No. 12/250,792 filed Oct. 14, 2008.

LICENSE RIGHTS-FEDERAL SPONSORED

The U.S. Government has a paid-up license in this invention and the right in limited circumstances to require the patent owner to license others on reasonable terms provided for by the terms of grant numbers 5R44NS043816, 1R43NS071882, and 7R43NS065554 awarded by the National Institutes of Health, National Institute of Neurological Disorders and Stroke and grant number 5R43AG033947 awarded by the National Institutes of Health, National Institute on Aging.

TECHNICAL FIELD

The present invention relates to diagnostic medical apparatus, systems, devices and/or methods, and more particularly, to apparatus and methods for quantifying the severity of movement disorders and their symptoms, such as Parkinson's disease, tremor, bradykinesia, dyskinesia, and gait and balance disturbances.

BACKGROUND

The current standard in evaluating the severity of movement disorder symptoms is the Unified Parkinson's Disease Rating Scale (UPDRS). Patients are typically scored by a certified trained clinician during an office visit. The UPDRS includes a number of tests used to score movement disorders, many of which involve repetitive movement tasks such as touching the nose and drawing the hand away repeatedly, or rapidly tapping the fingers together. Each test is evaluated by a clinician based solely on visual observation and graded on a scale that ranges from 0 (normal) to 4 (severe disorder). Even though numerical values are assigned, UPDRS scores are qualitative assessments and have been shown to vary considerably both between different evaluators of the same test and between the same evaluator's assessment of the same test scored at different times. The subjective assignment of UPDRS scores may mean that two experienced clinicians may assign greatly differing score values to a patient's performance of a test, even if the two clinicians base their scores on the same videorecorded performance. Even more troubling, the same clinician may assign greatly differing scores when making an assessment from the same videorecorded test viewed at different times. Additionally, while the UPDRS standard calls only for the assignment of discrete-integer score values (0, 1, 2, 3, or 4, for normal, slight, mild, moderate, and severe), some clinicians assign scores further specified by decimal fractions (2.3 or 3.5, e.g.), complicating diagnosis by assigning score values for which there is no universally agreed-upon significance. Specifically, bradykinesia-related items have the lowest reliability among all UPDRS items.

In addition to the UPDRS, the Movement Disorder Society has developed their own version of the UPDRS, the MDS-UPDRS. The MDS-UPDRS was designed to address weaknesses of the UPDRS such as ambiguities in scale descriptors and poor rating uniformity between clinicians. Despite addressing these issues, many of the weaknesses from the original UPDRS remain. Although the MDS-UPDRS maybe more descriptive, ratings remain on a discrete-integer 0-4 scale as described above. Such a discrete scale affirms the inherent variance of subjective independent clinician ratings, continuing to complicate diagnosis. Moreover, insightful gauging of movement disorder symptoms from the interpretation of a single examination, particularly in patients with motor fluctuations, is not as efficacious as would be periodic, objective monitoring of symptoms, particularly if such monitoring could be conducted at home.

Because prescribed treatments, including dosages of dopaminergic pharmacological drugs such as levodopa, many times are based in part on these scores, the evaluation of the efficacy of treatment protocols and the improvement of overall patient management is dependent upon the meaningfulness and reliability of scores assigned to assess movement disorder symptoms and thus upon the objectivity, accuracy, resolution, and frequency of the measurements upon which the scores are based.

One currently-marketed system for quantifying Parkinson's disease symptoms, that of Motus Bioengineering Inc., uses a miniature gyroscope to measure rotational motion on a hand and a data acquisition system to send measured rotational motion data to a processor. The processor then computes several simple statistics such as displacement and peak frequency. Another currently-marketed system, that of FlexAble Systems, Inc., uses a miniature 3-axis accelerometer to measure linear acceleration on a hand and a data acquisition system to send measured linear acceleration data to a processor. The processor then likewise computes several simple statistics such as weighted mean frequency of tremor, frequency spread, tremor amplitude and percent tremor time, and further computes a simple score by multiplying these statistics together. However, neither system is capable of providing a score that approximates or is predictive of a score given on the Unified Parkinson's Disease Rating Scale, and further, neither system is capable of providing a score that is based in part on reference data or uses an algorithm that has been trained from reference data consisting of UPDRS scores given by clinicians.

U.S. patent application Ser. No. 11/030,490 of Klapper, filed Jan. 5, 2005, herein incorporated by reference, describes a system of five accelerometers placed in different positions over the entirety of the body of a Parkinson's patient to acquire movement measurements and thereby stage, or classify movement states of, patients exhibiting bradykinesia and dyskinesia by continuously collecting data over extended time spans (hours or days). A test that can be administered rapidly, for example, in just a few minutes, would be preferable to the one described in the application of Klapper, as it could be performed either at home or in a brief visit to a doctor's office. Further, use of a small number of judiciously-placed sensors, or a system capable of detecting body movements without the placement of sensors on the body, would be less cumbersome for a subject than is placing sensors in a large number of locations, and would therefore have the advantage of being more readily acceptable. A test capable of quantifying the symptoms of bradykinesia, dyskinesia, and tremor is also more desirable than a test capable of evaluating only a subset of these common movement disorders. The quantification algorithm described in the application of Klapper describes prediction of a patient's self-assessment scores, but the capability to generate scores that correlate to UPDRS scores of trained clinicians would be the more valuable determination.

Two publications of Arash Salarian et al. ("An ambulatory system to quantify bradykinesia and tremor in Parkinson's disease," *Information Technology Applications in Biomedicine*, 2003, 4*th International IEEE EMBS Special Topic Conference on*, 2003, pp. 35-38, and "Quantification of tremor and bradykinesia in Parkinson's disease using a novel ambulatory monitoring system," *IEEE Transactions on Biomed Engineering*, Vol. 54, No. 2, February 2007, pp. 313-22) describe a wrist-mounted, 2-gyroscope-based system for quantifying tremor and bradykinesia in Parkinson's disease patients, and report correlation with UPDRS scores. However, this UPDRS tremor correlation was computed by combining rest and postural scores, whereas computing correlations for the scores separately, or components of the scores separately, is essential to determining valid correlations with UPDRS scores given for the different tests on the UPDRS motor exam. As with the system described in Klapper, the system of Salarian examines data from continuous long-term recordings, and requires over 5 minutes of recorded data to produce significant correlations. A preferred system would record data for individual tests given in only 15-20 seconds. The worn apparatus of the system described by Salarian weighs 35 grams, or 50 grams with a data logger for wireless operation, whereas a preferred worn apparatus would weigh less than 15 grams, or, ideally, less.

It is therefore the object of the present invention to provide a method and system for objectively quantifying movement disorder manifestations by providing symptom scores that are readily comprehensible to clinicians as being in the same scale as, and substantially correlative to, scores given on the Unified Parkinson's Disease Rating Scale. This method should eliminate clinician subjectivity while providing quantitative scores of improved resolution. It is further the object of the present invention to provide such a method and system with improved time and frequency resolution that will aid in evaluating efficacy of treatment protocols and improve patient management. It is yet further the object of the present invention to provide such a method and system used to recommend a treatment or a treatment adjustment, or to directly control treatment in an automated closed-loop treatment system. Predicate to all the above, it is the object of the present invention to record movement data from subjects as they complete motor tasks, process that data into quantitative kinematic features that describe movement disorder symptom severity, and use those kinematic features as inputs to a trained algorithm to output scores highly correlated to clinician scores of standardized movement disorder rating scales, such as the UPDRS.

As the Unified Parkinson's Disease Rating Scale is broadly taught, accepted and practiced by clinicians, the movement disorder quantification system of the present invention advantageously produces scores that approximate or mirror reliable UPDRS scores, promoting ready acceptance of the invention as an improved standard for patient diagnosis, monitoring, and treatment.

SUMMARY

The present invention relates to methods for quantifying movement disorders for the diagnosis and treatment of patients who exhibit the symptoms of Parkinson's disease and the like. The present invention further relates to an algorithm trained using reference data, particularly where the data comprises clinician-assigned movement disorder test scores given on the Unified Parkinson's Disease Rating Scale, and more particularly when the scores are given for tests from the UPDRS motor examination. The present invention further relates to the use of an algorithm trained using reference data, particularly where the data comprises former patient data.

Objective quantification of a subject's movement disorder symptoms, including tremor, bradykinesia, dyskinesia, and gait and balance disruptions for this invention, requires as a first step measurement of the movement. This measurement can be performed by measuring a single parameter or different parameters; the parameter or parameters being measured may include linear or rotational displacement, velocity, or acceleration, electromyographic (EMG) signals, or any other parameter that could give a quantitative indication of motion; and the part of the body being measured for motion may be a limb (as at a wrist, ankle, heel, thigh, or finger) or may be the trunk of the body (as at a shoulder, waist, or torso) and by other techniques known to those skilled in the art. Sensors used for measuring body motion include gyroscopes and accelerometers, preferably miniaturized; electromagnets; EMG; video; load cells; or other sensors known to those skilled in the art. Other systems that can be used to detect and measure body motion include motion capture systems, machine vision systems, sonic or laser Doppler velocity transducers, infrared systems, GPS, force transduction systems, or any other system known to those skilled in the art.

The movement data acquisition system, or "movement measuring apparatus," used in the present invention may incorporate one or more of any of the above sensors or systems. A pre-existing movement data acquisition system, such as the one described in patent application Ser. No. 11/082,668, herein incorporated by reference, may similarly be used. In the present disclosure, "movement data" is construed as including, but not being limited to, any signal or set of signals, analog or digital, corresponding to movement of any part of the body or multiple parts of the body, independently or in conjunction with each other. Movement may be continuously measured over long time spans, or may be measured over a short time span, for example, during the period of performing one or several tests taken from or modified from the UPDRS, MDS-UPDRS, or other motor exams. In certain embodiments of the present invention, the measurement time needed to produce a score substantially predictive of a UPDRS score for a given test on the UPDRS motor exam or to produce a score that represents an independent component of a symptom of a movement disorder is acquired during a test lasting no more than about 20 seconds. Further, in certain embodiments of the present invention, for example, the measurement time needed to produce scores substantially predictive of a set of multiple UPDRS scores for multiple given tests on the UPDRS motor exam is acquired during a test preferably lasting no more than about 30 minutes. Likewise, other motor exams may take similar or shorter periods of time to test a subject. More preferably, the measurement time does not exceed 15 minutes. More preferably, the measurement time does not exceed 10 minutes. Even more preferably, the measurement time does not exceed 5 minutes. Even still more preferably, the measurement time does not exceed 3 minutes. Even still more preferably, the measurement time does not exceed 1 minute. Still more preferably, the measurement time does not exceed 15-30 seconds.

Following measurement of symptomatic movement, the next step in objective quantification of a subject's movement disorder symptoms is the extraction of statistical kinematic features from the acquired movement data via computer processing. This processing may take place during or following data acquisition and may occur within a movement data acquisition device or within a different processing device. Such external devices may include a server, personal computer, PDA, smart phone, portable tablet, or the like, and may use one or a number of computer processors with which the acquisition device interfaces, either through a cable or tethered connection or by wireless transmission. Processing may, for example, involve analog to digital conversion of raw gyrometric or accelerometric data, filtering of the digital data to appropriate biological ranges, storage or transmission of the data in various data states to internal memory (such as RAM, SD, flash memory, or the like) or an external device (such as servers, personal computer, PDA, smart phone, portable tablet, or the like), extraction of kinematic features, application of scoring algorithms, or any other steps that would be readily apparent to those skilled in the art.

Useful kinematic features that may be extracted from gyroscopic data may include, for example, peak power angular velocity, peak power angle, log of the peak power angular velocity, log of the peak power angle, RMS of the log peak power, RMS angular velocity, log of the RMS angular velocity, frequency, maximum amplitude, maximum peak-to-peak amplitude, zero crossings, mean angular velocity, maximum angular velocity, excursion angle, and wavelet parameters, as well as the covariance, coefficient of variation, or standard deviation over time of any of these parameters. Useful kinematic features that may be extracted from accelerometer data may include, for example, peak power acceleration, peak power velocity, peak power position, RMS acceleration, RMS velocity, RMS position, frequency, maximum amplitude, maximum peak-to-peak amplitude, mean acceleration, and wavelet parameters, as well as the covariance, coefficient of variation, or standard deviation over time of any of these parameters. In a movement data acquisition system, or movement measuring apparatus, that combines three-axes of accelerometer data and three-axes of gyroscope data to produce 6 channels or vector of movement data, one or any combination of the above kinematic features can be extracted from any of the 6 kinematic vectors or channels to be used as inputs to a trained algorithm in the next step. The listed kinematic features for the sensors above are intended to be exemplary, and not limiting; other types of sensors will produce different data from which different sets of features may be extracted.

The training algorithm preferably used to process the kinematic features extracted from the movement data may comprise, for example, one or more of a simple or multiple linear regression, an artificial neural network, a Bayesian network, or a genetic algorithm. Other algorithms that can be used to enhance the analysis include but are not limited to wavelet analysis, fast Fourier transforms, optimization technics and the like. The output of the trained algorithm may be a single score or multiple scores of any scale; a single score on the same scale as that of the UPDRS may be preferred in certain applications where simplicity or familiarity is the paramount concern, while more sophisticated scores and scales may be preferred for other advanced applications, such as those that score individual components of a movement disorder or that involve recommendations for treatment or closed-loop automated treatment delivery.

A number of embodiments of the present invention are envisioned in this disclosure. The following are examples of these embodiments but in no way limit the numerous other embodiments that are encompassed by this patent application.

In one embodiment, the system for quantifying movement disorder symptoms of the present invention comprises a movement measuring apparatus to acquire data corresponding to movement of the body of a subject, a processor capable of processing the acquired movement data with an algorithm for calculating a score based at least in part on the movement data, where the algorithm is based at least in part on reference data, and, optionally, a display showing the score. The reference data may comprise UPDRS scores given by preferably at least two trained clinicians, and the score may be limited to real number values between 0 and 4, inclusive.

In another embodiment, the present invention constitutes a method for quantifying symptoms of a movement disorder of a subject, comprising measuring the movement of a subject's limb to acquire movement data, processing the movement data to extract at least one kinematic feature, and processing the at least one kinematic feature using a trained algorithm to determine a score, where the algorithm is trained using reference data that includes UPDRS scores given by at least two clinicians, and where the score is used for the diagnosis or treatment of the subject.

In yet another embodiment, the system for quantifying movement disorder symptoms of the present invention comprises a movement measuring apparatus to acquire data corresponding to movement of the subject, a processor capable of processing the acquired movement data with an algorithm for calculating a score based at least in part on the movement data, where the algorithm is based at least in part on reference data that includes UPDRS scores given by at least two clinicians, and an output of a signal corresponding to a recommendation for treatment, where said recommendation is derived at least in part from the processed movement data.

In yet another embodiment, the system for quantifying bradykinesia of a subject having a movement disorder of the present invention comprises at least two types of sensors to acquire movement data corresponding to movement of the subject, and a processor capable of processing the acquired movement data with an algorithm for calculating an independent disorder component score based at least in part on the movement data, where the algorithm is trained at least in part on reference data and the score represents amplitude, speed, or rhythm of the symptom of the movement disorder.

In yet another embodiment, the present invention constitutes a method for quantifying symptoms of a subject having a movement disorder, comprising measuring movement of a subject to acquire movement data during a given standardized clinical task, processing the movement data to extract at least one kinematic feature, and processing with a computer processor the at least one kinematic feature using a trained algorithm to determine a score for an independent component of the movement disorder, where the algorithm is trained at least in part on reference data and the score is significantly correlated to amplitude, speed, or rhythm of the movement disorder.

In yet another embodiment, the system for quantifying gait and balance of a subject having a movement disorder of the present invention comprises at least two types of sensors to acquire movement data during a given standardized clinical diagnostic task, and a processor capable of processing the acquired movement data with an algorithm for calculating a score based at least in part on the movement data, where the algorithm is trained at least in part on reference data and the score is correlated to a score given by a skilled clinician using the UPDRS or MDS-UPDRS.

Preferably, the movement measuring apparatus is small, lightweight, and not cumbersome. In some embodiments of the present invention, the movement measuring apparatus preferably consists only of one or two sensor packages placed only on the wrist and finger of the subject and weighs no more than about 3.4 ounces. More preferably, the movement measuring apparatus consists of a sensor package placed only on the finger of the subject and weighs no more than half an ounce. Most preferably, the movement measuring apparatus weighs no more than 10 grams. In other embodiments, preferably the movement measuring apparatus is machine vision-based and uses a video camera or similar sensor to detect the motion of the subject without any sensor devices placed on the body of the subject.

This patent application herein incorporates by reference U.S. patent application Ser. No. 11/082,668 filed Mar. 17, 2005; Ser. No. 11/432,583 filed May 11, 2006; and Ser. No. 12/250,792 filed Oct. 14, 2008.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DESCRIPTION OF THE PREFERRED EMBODIMENTS

Figure 1A:
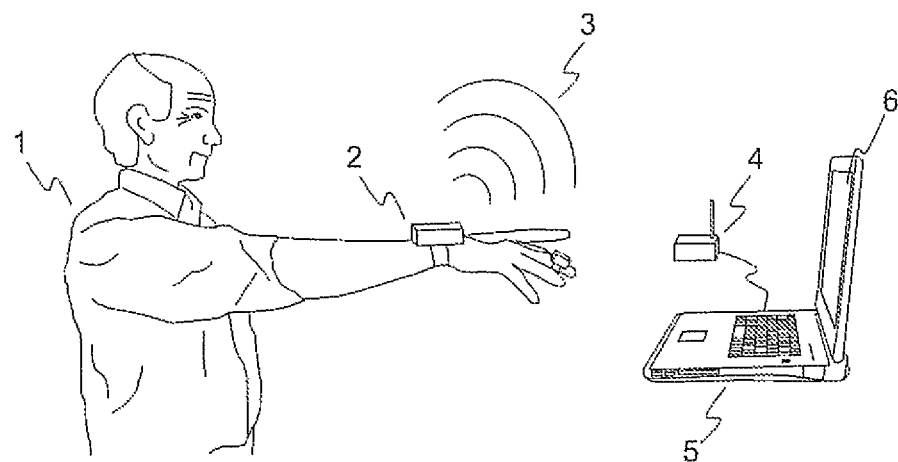
FIG. 1. Schematic views of subject kinematics being measured with movement measuring apparatus in two different embodiments of the present invention.

The present invention relates to the quantification of movement disorders in a movement disorder monitor, and a method of objectively quantifying the severity of a subject's movement disorder. Preferably, this quantification is reduced to a simple score on a scale equivalent to that of the UPDRS. The present invention additionally relates to the use of such quantification to provide recommendation in diagnosis of the subject's movement disorder, for treatment or as part of a treatment delivery system for automatically dosing a subject with a pharmaceutical drug, or for supplying some part of the nervous system of the subject with an electrical stimulus in response to the quantified level of severity of a subject's symptoms.

The systems and methods of the various embodiments of the present invention are used to analyze, score, and treat various movement disorders. Movement disorders and their symptoms for purposes of this application include but are not limited to Parkinson's disease, essential tremor, bradykinesia, dyskinesia, and gait and balance disturbances. Some of the treatments used for these disorders involve physical therapy, pharmaceutical interventions, fetal cell transplants, surgery, or deep brain stimulation. The efficacy of these interventions is often judged by the intervention's ability to alleviate subject symptoms and improve subject quality of life. The subject on which system or method is used is a human or another form of animal.

The present invention includes trained algorithms to determine scoring from movement data acquired by a movement measuring apparatus. The trained algorithm in part comprises a mathematical model or quantitative representation, used to process kinematic features computed from the movement data and may include some of those steps known to those skilled in the art. In the development of one of the algorithms of the present invention, a movement data acquisition system comprising a three-axis accelerometer and a three-axis gyroscope was used to collect data from 60 Parkinson's disease subjects as they completed a subset of the UPDRS upper extremity motor exam including rest, postural, and kinetic tremor. For some patients, each arm was tested once when symptoms were occurring. In others, the more affected arm was tested twice, once with and once without symptoms. For this group, symptoms were controlled by timing of medication or turning on and off deep brain stimulation. In all, 87 total trials were performed with a variety of patient tremor symptoms.

Subjects were videotaped and rated on the UPDRS (0-4) by two movement disorder neurologists. Their two scores were averaged.

The six kinematic signals were band pass filtered to 3-10 Hz using a second-order Butterworth filter. The power spectrum of each signal was calculated using an FFT. Several time- and frequency-based measures were computed for each channel of movement data including the peak power, frequency of the peak power, root mean square (RMS) of the angular velocity, and RMS of the angle.

A multiple linear regression model was used to correlate quantitative kinematic features of the kinematic signals with the average clinician UPDRS score for each tremor task. The following linear model was used to regress the average clinician scores against the computed quantitative variables:

$$R = b_0 + \vec{B}_a \cdot \vec{P}_a + \vec{B}_g \cdot \vec{P}_g \quad (1)$$

where R is the clinician's score and $\vec{B}_a$, $\vec{B}_g$, $\vec{P}_a$, and $\vec{P}_g$ are all 3-dimensional vectors. $\vec{P}_a$ and $\vec{P}_g$ are the quantitative variables for the three accelerometers and three gyroscopes, respectively, $\vec{B}_a$, $\vec{B}_g$, and $b_0$ are the regression coefficients, and · is the dot product operator. This model can be rewritten as:

$$R = b_0 + B_{ax}P_{ax} + B_{ay}P_{ay} + B_{az}P_{az} + B_{gx}P_{gx} + B_{gy}P_{gy} + B_{gz}P_{gz} \quad (2)$$

Out of all the kinematic features examined, logarithm of the peak power for all six channels correlated best for rest and postural tremor, while the RMS amplitude of all six channels correlated best for kinetic tremor.

The values of $\vec{B}_a$, $\vec{B}_g$, and $b_0$ that were determined from the regression (EQ. 1) for each task can now be used in the algorithm to generate scores: data can be recorded by the movement measuring apparatus and processed to extract kinematic features $\vec{P}_a$ and $\vec{P}_g$, which values are then input back into EQ. 1 to get R, the generated score. (Scores below 0 or above 4 are rounded to 0 or 4, respectively.)

Figure 1B:
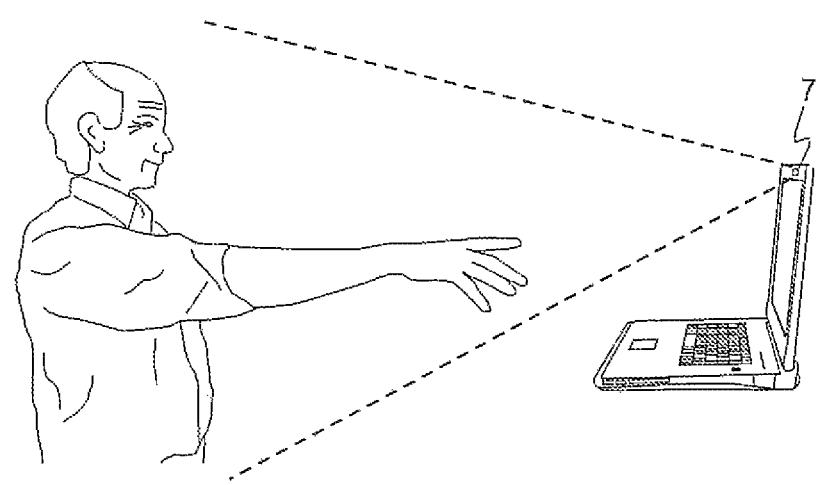

FIG. 1 shows the data collection process for two different embodiments of the present invention. In FIG. 1a, a subject 1 wears a sensor unit 2 comprising accelerometers and gyroscopes (both not shown) as well as a transmission system (not shown). The transmission system may be wired or wireless, and may communicate via any medium and any transmission protocol known to someone skilled in the art. In the illustrated embodiment, the subject 1 performs a movement disorder test according to instructions and, optionally, an instructional video displayed on a monitor 6 and/or according to instructions given by a clinician. The sensor unit 2 transmits the subject's movement data via radio link 3 to a receiver unit 4, which is plugged into a computer 5 via USB. The processor of the computer 5 processes the movement data to extract kinematic features which are then fed into a trained algorithm implemented as a software algorithm in the computer 5. The trained algorithm outputs a score which may then be displayed on the monitor 6. The processor may also create an output to a treatment device (not shown), which output is used to control such device. FIG. 1b) illustrates substantially the same process with a different form of movement measuring apparatus. In FIG. 1b), a camera 7, which may be a webcam built into a computer (as illustrated) or may be a separate camera or set of multiple cameras (not shown) connected to a computer, which view the subject performing the motion disorder test and feeds video data into the computer where, for example, machine vision algorithms measure the motion of the limbs of the subject with respect to time according to any method known in the art. Such a method may consist, for example, in determining marker points along the limb of the subject in order to gauge relative motion, and such a method may be assisted by applying more visible markers (not shown) on various points on the limb of a subject, such as is common with motion capture technology. Thus in FIG. 1b) the need for sensor unit 2 of FIG. 1a), with its accelerometers and gyroscopes, is obviated.

Figure 2:
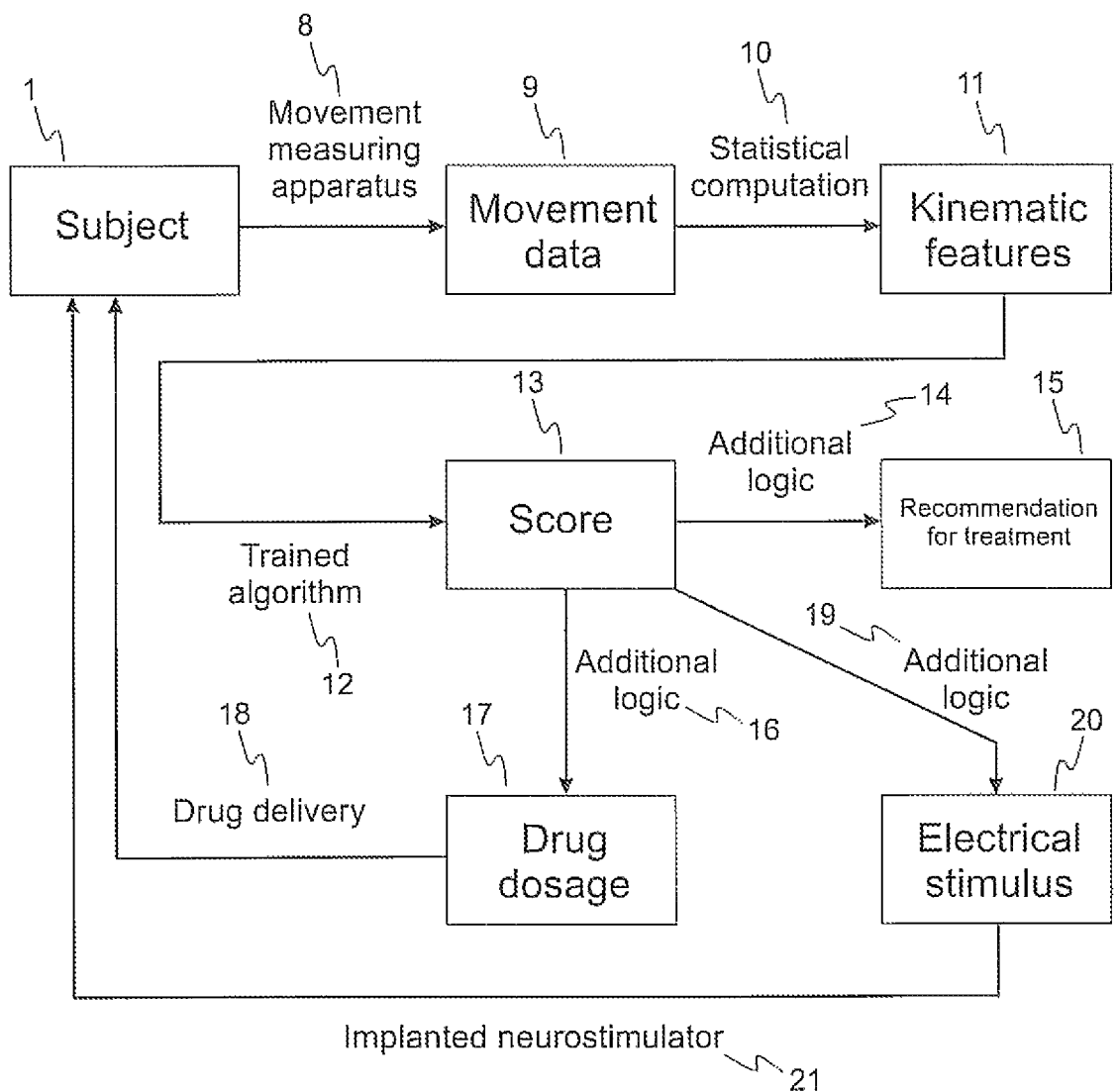
FIG. 2. Flow diagram of the quantification system in one embodiment of the present invention.

FIG. 2 shows one process of score calculation as a flow diagram. The movement measuring apparatus 8 may be of any type described above or any other type known to those skilled in the art. Movement data 9 are acquired from the subject 1 by the movement measuring apparatus 8. Kinematic features 11, extracted from the movement data 9 through statistical computation 10 inside a processor, are fed into a trained algorithm 12, which may be of any type described in this disclosure or of another type known to those skilled in the art, to determine the score 13. Where a score on the Unified Parkinson's Disease Rating Scale is desired, this score is a real number between 0 and 4, inclusive. Certain additional logic 14 may generate from the score 13 a recommendation for treatment 15, while other additional logic 16 may determine a drug dosage 17 administered to the patient 1 through a drug delivery system 18 (e.g., an implantable pump), and still other additional logic 19 may determine the parameters for an electrical stimulus 20 administered to the patient 1 via an implanted neurostimulator 21 (a deep brain stimulation electrode probe, e.g.).

In the development of another algorithm used in various embodiments of the present invention, three axes of accelerometer data and three axes of gyroscopic data were collected from 50 Parkinson's disease patients on and off medication as they completed a subset of the UPDRS and MDS-UPDRS repetitive motion exams including finger tapping, hand grasping, and pronation-supination tasks. The tasks were performed on the more affected limb for 15 seconds with as large an amplitude and as fast movements as possible. Subjects were videotaped while performing these tasks and then rated according to the UPDRS and MBRS by four neurologists in order to obtain independent scores for amplitude, speed, and rhythm. MBRS is the modified bradykinesia rating scale, and was developed to independently rate speed, amplitude and rhythm components of bradykinesia. The MBRS scale is described in more detail in Kishore, et al., "Unilateral versus bilateral tasks in early asymmetric Parkinson's disease: differential effects on bradykinesia", *Movement Disorders*, 2007; 22:328-333, which is herein incorporated by reference. The six kinematic signals were band pass filtered to 3-10 Hz using a second-order Butterworth filter. The power spectrum of each signal was calculated using an FFT. Several time- and frequency-based measures were computed for each channel of movement data including the log of the RMS of angular velocity, RMS of the RMS of excursion angle, and the coefficient of variation.

A multiple linear regression model was used to correlate quantitative kinematic features of the kinematic signals with the average clinician MBRS score for each bradykinesia task. The following linear model was used to regress the average clinician scores against the computed quantitative variables:

$$R = b_0 + b_1 \cdot \vec{P} \qquad (3)$$

where R is the clinician MBRS score, P is one of processed kinematic feature that varies for the three MBRS subscores, $b_0$ and $b_1$ are the regression coefficients, and · is the dot product operator.

Of the kinematic features examined, log of RMS angular velocity correlated best to the speed component, RMS excursion angle correlated best with amplitude, and the coefficient of variation correlated best with rhythm. The values determined from the regression for $b_0$ and $b_1$ can now be used in the algorithm to generate scores for each component during a given task.

The development of yet another embodiment of the present invention, rating gait and balance disturbances of a movement disorder, followed a similar method as that used to find EQ. 3, and therefore follows the same structure as EQ 3. Subjects were asked to perform the following UPDRS and MDS-UPDRS tasks correlating to gait and balance disturbances while wearing sensor units comprising tri-axial accelerometers and tri-axial gyroscopes: (1) toe tapping, (2) leg agility, (3) arising from chair, (4) gait, (5) freezing of gait, (6) postural stability, and (7) posture. Any set of the above tasks, or other tasks known by those skilled in the art as diagnostic tasks for gait and balance disturbances, such as those defined by standardized scales like the UPDRS and MDS-UPDRS could be used in the algorithm training process. Subjects were videotaped performing the tasks and given scores according to the UPDRS and MDS-UPDRS by trained clinicians. The model of EQ. 3 was then used to regress the average clinician score for each task against computed quantitative variables.

Figure 3:
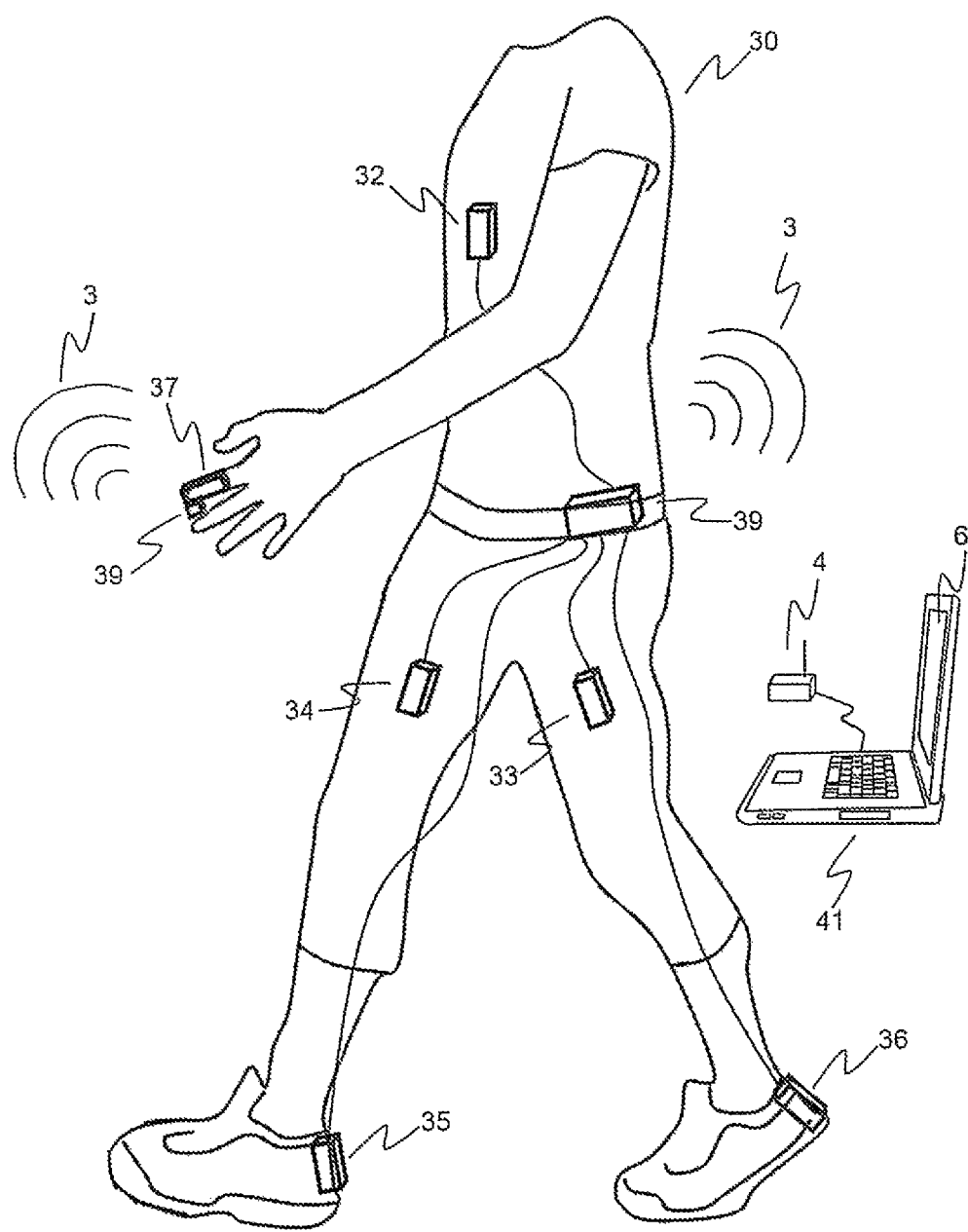
FIG. 3. Schematic view of a subject showing possible sensor units comprising accelerometers and gyroscopes in different embodiments of the present invention.

Of the kinematic features examined, heel speed, log of peak power angular velocity of the subject's heel correlated best to toe tapping; heel speed, RMS of the magnitude of linear velocity of the subject's heel correlated best to leg agility; gyroscopic zero crossings of the subject's torso correlated best to arising from a chair; heel speed, RMS of the log gyroscopic peak power correlated best to gait; turn time correlated best to freezing of gait; heel accelerometer measurement of steps taken correlated best to postural stability; and angle of torso inclination correlated best to posture. Other kinematic features obtained from heel, thigh, or torso accelerometers and gyroscopes provided relevant correlations, such as, log of the heel peak power angle; coefficient of variation of heel angle; RMS of the magnitude of position for the heel and thigh accelerometers; coefficient of variation for RMS of the magnitude of position for the heel and thigh accelerometers; RMS of the magnitude of linear velocity of the thigh; time to complete a task; maximum of the angular torso velocity; mean linear acceleration for the torso; steps per minute; angular range of thigh and heel motion; time delay during a task; angle of neck inclination FIG. 3 shows possible sensor locations for different embodiments of the present invention. A subject 30 wears six sensor units 32-37 comprising accelerometers and gyroscopes (both not shown) for recording movement data. Preferably, the subject 30 wears at least one sensor unit on a heel 35-36, thigh 33-34, finger 37, or torso 32. More preferably, the subject 30 wears at least 2 sensor units on a combination of heels 35-36, thighs 33-34, fingers 37, or a torso 32. Even more preferably, the subject 30 wears at least 4 sensor units on a combination of heels 35-36, thighs 33-34, fingers 37, or a torso 32. Still even more preferably the subject 30 wears at least 8 sensor units on a combination of heels 35-36, thighs 33-34, fingers 37, joints (not shown), upper appendages (not shown), a waist (not shown), a torso 32, or other useful recording position known to someone skilled in the art. Additionally, an internal processing unit 39 for handling the movement data may be wired or wireless with respect to both the sensors and an external processing unit 41. The movement data from the internal processing unit is either stored for later transfer or immediately transmitted to a receiver unit 4 on the external processing unit via any medium and any transmission protocol, for example, radio link 3, Bluetooth, WIFIUSB (not shown), or the like. The processor (not shown) of the external processing 41 unit feeds the data into a trained algorithm implemented as a software algorithm. The trained algorithm outputs a score which may then be displayed on a monitor 6 or to control a treatment device (not shown).

Figure 4:
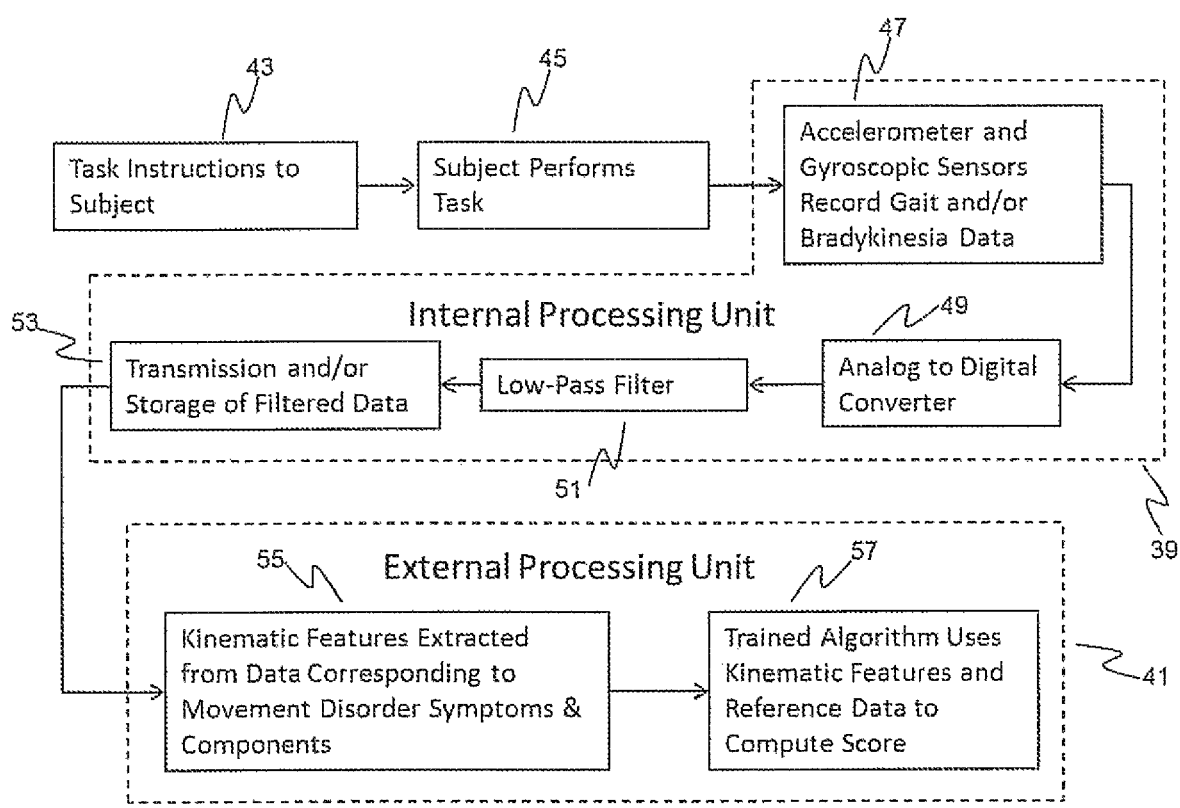
FIG. 4. Flow diagram of the processes involved in quantification of component data in one embodiment of the present invention.

FIG. 4 shows one process of score calculation as a flow diagram. Task instructions are given to a subject 30 and may comprise any of the tasks described above, or any task used to measure movement disorders by those skilled in the art. As the patient performs the tasks 45, accelerometers and gyroscopes of sensor units 32-37, such as those described in FIG. 3 or others known to those skilled in art, measure the subject's movement data 47. The internal processing unit 39 digitizes the measured movement data 49 at 128 Hz using an analog to digital converter. A 20 Hz low pass filter 51 then removes any noise or other high frequency information that is not associated with actual movement data. The filtered digital movement data is then stored for later transfer or immediately transmitted 53 for processing by the external processing unit 41. The digital data may be stored using internal memory such as RAM, SD, flash memory, or the like, and later transmitted to the external processing unit 41 through a wired connection such as USB (not shown), or wireless protocols such as a radio link 3, Bluetooth, WiFi, or the like. The data may also be transmitted through wired or wireless protocols by any type known to those skilled in the art during recording and internal processing. Once the data reaches the external processing unit 41, a computer processor of the external processing unit (not shown) extracts kinematic features from the digital data corresponding to movement disorders and their components 55. The kinematic features may be those described above, or any known by those skilled in the art to best correlate with particular movement disorder symptoms or components. These kinematic features are then fed to a trained algorithm to compute a final score 57 corresponding to the disorder or component tested for. This score may then be used in additional treatment and diagnosis logic as described above.

The movement disorder quantification system of the present invention can be tested for accuracy. According to one test method, movement data is collected from subjects with Parkinson's disease using the system while performing the standard upper extremity UPDRS motor exam, and the test is simultaneously scored, or videorecorded for subsequent scoring, by one or more skilled clinicians. Scores from multiple clinicians for the same subject's test may be combined or aggregated by averaging, weighted averaging, or any other known method. A linear regression may then be performed with the system scores as the predictor variable values and the clinician scores as the response variable values. The coefficient of determination ($R^2$) computed from the linear regression and the root-mean-square (RMS) error between the system scores and the averaged clinician scores then serve as measures of system reliability.

The reliability test itself becomes more reliable when the number of motor exam test scores collected is large, and when the number of clinician scores for each test is large. Preferably, scores from at least 60 motor exam tests are collected. More preferably, scores from at least 100 motor exam tests are collected. Still more preferably, scores from at least 200 motor exam tests are collected. Because of the variability between scores given by different skilled clinicians, it is important that the reference data used to train the system and method of the present invention does not rely on the scoring of only one clinician. Therefore, these motor exam tests are each scored by at least 2 skilled clinicians. Preferably, these tests are each scored by at least 5 skilled clinicians. More preferably, these tests are each scored by at least 7 skilled clinicians. For the purposes of this disclosure, the terms "skilled clinician" and "trained clinician," used interchangeably, refer to those clinicians who have received accreditation in UPDRS scoring from the Movement Disorders Society (as described in Goetz and Stebbins, "Assuring interrater reliability for the UPDRS motor section: Utility of the UPDRS Teaching Tape", *Movement Disorders*, Vol. 19, No. 12, 2004, herein incorporated by reference), or the recognized equivalent.

Preferably, the coefficient of determination between the system scores and the averaged clinician scores for the rest tremor portion of the motor exam is greater than about 0.6. More preferably, the coefficient of determination between the system scores and the average clinician score for the rest tremor portion of the motor exam is greater than about 0.7. Even more preferably, the coefficient of determination between the system scores and the average clinician score for the rest tremor portion of the motor exam is greater than about 0.8. More preferably still, the coefficient of determination between the system scores and the average clinician score for the rest tremor portion of the motor exam is greater than about 0.85. Even more preferably, the coefficient of determination between the system scores and the average clinician score for the rest tremor portion of the motor exam is greater than about 0.9. Still more preferably, the coefficient of determination between the system scores and the average clinician score for the rest tremor portion of the motor exam is greater than about 0.95. Most preferably, the coefficient of determination between the system scores and the average clinician score for the rest tremor portion of the motor exam is greater than about 0.98.

Preferably, the coefficient of determination between the system scores and the averaged clinician scores for the postural tremor portion of the motor exam is greater than about 0.6. More preferably, the coefficient of determination between the system scores and the average clinician score for the postural tremor portion of the motor exam is greater than about 0.7. Even more preferably, the coefficient of determination between the system scores and the average clinician score for the postural tremor portion of the motor exam is greater than about 0.8. More preferably still, the coefficient of determination between the system scores and the average clinician score for the postural tremor portion of the motor exam is greater than about 0.88. Even more preferably, the coefficient of determination between the system scores and the average clinician score for the postural tremor portion of the motor exam is greater than about 0.9. Still more preferably, the coefficient of determination between the system scores and the average clinician score for the postural tremor portion of the motor exam is greater than about 0.95. Most preferably, the coefficient of determination between the system scores and the average clinician score for the postural tremor portion of the motor exam is greater than about 0.98.

Preferably, the coefficient of determination between the system scores and the averaged clinician scores for the kinetic tremor portion of the motor exam is greater than about 0.4. More preferably, the coefficient of determination between the system scores and the average clinician score for the kinetic tremor portion of the motor exam is greater than about 0.5. Even more preferably, the coefficient of determination between the system scores and the average clinician score for the kinetic tremor portion of the motor exam is greater than about 0.6. More preferably still, the coefficient of determination between the system scores and the average clinician score for the kinetic tremor portion of the motor exam is greater than about 0.7. Even more preferably, the coefficient of determination between the system scores and the average clinician score for the kinetic tremor portion of the motor exam is greater than about 0.8. Even more preferably, the coefficient of determination between the system scores and the average clinician score for the kinetic tremor portion of the motor exam is greater than about 0.9. Still more preferably, the coefficient of determination between the system scores and the average clinician score for the kinetic tremor portion of the motor exam is greater than about 0.95. Most preferably, the coefficient of determination between the system scores and the average clinician score for the kinetic tremor portion of the motor exam is greater than about 0.98.

Preferably, the RMS error between the system scores and the averaged clinician scores for the rest tremor portion of the motor exam is less than about 15%. More preferably, the RMS error between the system scores and the averaged clinician scores for the rest tremor portion of the motor exam is less than about 10%. Even more preferably, the RMS error between the system scores and the averaged clinician scores for the rest tremor portion of the motor exam is less than about 9%. More preferably still, the RMS error between the system scores and the averaged clinician scores for the rest tremor portion of the motor exam is less than about 8%. Even more preferably, the RMS error between the system scores and the averaged clinician scores for the rest tremor portion of the motor exam is less than about 5%.

Preferably, the RMS error between the system scores and the averaged clinician scores for the postural tremor portion of the motor exam is less than about 15%. More preferably, the RMS error between the system scores and the averaged clinician scores for the postural tremor portion of the motor exam is less than about 10%. Even more preferably, the RMS error between the system scores and the averaged clinician scores for the postural tremor portion of the motor exam is less than about 9%. More preferably still, the RMS error between the system scores and the averaged clinician scores for the postural tremor portion of the motor exam is less than about 8%. Even more preferably, the RMS error between the system scores and the averaged clinician scores for the postural tremor portion of the motor exam is less than about 5%.

Preferably, the RMS error between the system scores and the averaged clinician scores for the kinetic tremor portion of the motor exam is less than about 20%. More preferably, the RMS error between the system scores and the averaged clinician scores for the kinetic tremor portion of the motor exam is less than about 15%. Even more preferably, the RMS error between the system scores and the averaged clinician scores for the kinetic tremor portion of the motor exam is less than about 11%. More preferably still, the RMS error between the system scores and the averaged clinician scores for the kinetic tremor portion of the motor exam is less than about 10%. Even more preferably, the RMS error between the system scores and the averaged clinician scores for the kinetic tremor portion of the motor exam is less than about 8%.

For tests designed to evaluate bradykinesia, such as finger taps, hand grasps, and rapid alternating hand movements, coefficient of determination values are preferably greater than about 0.5, even more preferably greater than about 0.6, even more preferably greater than about 0.7, even more preferably greater than about 0.8, and still more preferably greater than 0.9; and RMS errors are preferably less than about 15%, more preferably less than about 12%, even more preferably less than about 10%, even more preferably less than about 8%, and still more preferably less than about 6%.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A method for quantifying and treating symptoms of a subject having a movement disorder, comprising:
   measuring movement of a subject with a sensor to acquire movement data during a diagnostic task the subject is instructed to perform;
   processing the movement data from the diagnostic task the subject is instructed to perform to extract at least one kinematic feature;
   processing with a computer processor the at least one kinematic feature using a trained algorithm comprising a mathematical model adapted for processing kinematic features from movement data to determine a score for an independent component of a symptom of the movement disorder;
   outputting the independent component score, or data related to the independent component score, for display and/or use by a clinician or the subject as a measure of assessment of the movement disorder, or to adjust treatment parameters or settings of a treatment device; and adjusting the treatment parameters or settings of the treatment device and providing a treatment to the subject based at least in part on the outputted independent component score or data related to the independent component score, wherein the algorithm is trained at least in part on reference data and the score is significantly correlated to amplitude, speed, or rhythm of the symptom of the movement disorder.

2. The method of claim 1, wherein the symptoms of the movement disorder represent gait and balance disturbances.

3. The method of claim 1, wherein the diagnostic task the subject is instructed to perform is defined by the Unified Parkinson's Disease Rating Scale (UPDRS) or Movement Disorder Society UPDRS (MDS-UPDRS).

4. The method of claim 1, wherein the at least one kinematic feature is the log of the root mean squared angular velocity.

5. The method of claim 1, wherein the at least one kinematic feature is the excursion angle.

6. The method of claim 1, wherein the at least one kinematic feature is the root mean squared coefficient of variation.

7. The method of claim 1, wherein the at least two types of sensors comprise at least one sensor placed on a heel, thigh, or torso of the subject.

8. The method of claim 1, wherein the score for an independent component of a symptom is further used to generate a recommendation for treatment.

9. A method for quantifying and treating symptoms of a subject having a movement disorder, comprising:

measuring movement of a subject with a sensor to acquire movement data during a diagnostic task the subject is instructed to perform;

processing the movement data from the diagnostic task the subject is instructed to perform to extract at least one kinematic feature;

processing with a computer processor the at least one kinematic feature using a trained algorithm comprising a mathematical model adapted for processing kinematic features from movement data to determine a score for an independent component of a symptom of the movement disorder;

outputting the independent component score or data related to the independent component score for display and/or use by a clinician or the subject as a measure of assessment of the movement disorder, to adjust at least one drug dosage; and adjusting drug dosage and providing the adjusted drug dosage to the subject based at least in part on the outputted independent component score or data related to the independent component score, wherein the algorithm is trained at least in part on reference data and the score is significantly correlated to amplitude, speed, or rhythm of the symptom of the movement disorder.

10. The method of claim 9, wherein the symptoms of the movement disorder represent gait and balance disturbances.

11. The method of claim 9, wherein the diagnostic task the subject is instructed to perform is defined by the Unified Parkinson's Disease Rating Scale (UPDRS) of Movement Disorder Society UPDRS (MDS-UPDRS).

12. The method of claim 9, wherein the at least one kinematic feature is the log of the root mean squared angular velocity.

13. The method of claim 9, wherein the at least one kinematic feature is the excursion angle.

14. The method of claim 9, wherein the at least one kinematic feature is the root mean squared coefficient of variation.

15. The method of claim 9, wherein the score for an independent component of a symptom is further used to generate a recommendation for treatment.

\* \* \* \* \*